United States Patent [19]

Acree et al.

[11] Patent Number: 4,567,043
[45] Date of Patent: Jan. 28, 1986

[54] CANINE CORONA VIRUS VACCINE

[75] Inventors: William M. Acree; Bobby Edwards, both of Temple, Tex.; John W. Black, Milton, Tenn.

[73] Assignee: American Home Products Corporation (Del.), New York, N.Y.

[21] Appl. No.: 504,434

[22] Filed: Jun. 15, 1983

[51] Int. Cl.$^4$ .............................................. A61K 39/12
[52] U.S. Cl. ...................................................... 424/89
[58] Field of Search ............................... 435/235–239; 424/89

[56] References Cited

U.S. PATENT DOCUMENTS 3,143,474  8/1964  Froelich ............................ 435/237

OTHER PUBLICATIONS

Yasohima et al., Jpn. J. Vet. Sci., 45(2), 217–225 (1983).
Appel et al., The Cornell Veterinarian, 69(3), 123–133 (1979).
Benary et al., Kleintierpraxes, 26, 1–60, pp. 7–12 (1981).
Gill, Diss'n Abs. Intl., 43(8), Microbiology, 2452-B (Feb. 1983).
Keenan et al., Am. J. Vet. Res., 37(3), pp. 247–256, (Mar. 1976).
Helfer-Baker et al., Canine Practice, 7(3), pp. 37–42, (May-Jun. 1980).
Vandenberghe et al., Vet. Quarterly, 2(3), pp. 136–141 (Jul. 1980).
ATCC *Catalogue of Strains* II, 3rd Ed., p. 256, 1981.
Appel et al., Canine Practice, vol. 7, No. 4, pp. 22–34, (1980).
Appel et al., Neurology 31(8): 944–949, 1981.
Tingpalapong et al., Am. J. Vet. Res. 43(9): 1687–1690, 1982.
Woods, R. D. et al., Vet. Microbiol. 7(5): 427–436, 1982.
Horzinck et al., Infect. Immun. 37(3): 1148–1155, 1982.
Toma et al., Recl. Med. Vet. Ec. Alfort., 156(6): 464–470, 1980.
Garwes et al., J. Gen. Virol. 52(1): 153–158, 1981.
Binn et al., Am. J. Vet. Res. 42(10): 1665–1667, 1981.

*Primary Examiner*—Sidney Marantz
*Assistant Examiner*—Shawn P. Foley
*Attorney, Agent, or Firm*—Adley F. Mandel

[57] ABSTRACT

An efficacious parenterally administered modified live Canine Corona virus vaccine which provides systemic, humoral protection and also protection of the intestinal tract in dogs from infection by virulent Canine Corona virus is produced. A method for propagation of the Canine Corona virus and its attenuation and a method of evaluating the effectiveness of a Canine Corona virus vaccine in canines is also disclosed.

23 Claims, No Drawings

CANINE CORONA VIRUS VACCINE

BACKGROUND AND FIELD OF THE INVENTION

Canine Corona Virus (CCV) enteritis is a highly contagious disease in dogs with world-wide distribution. CCV gastroenteritis was first observed in February of 1970 in a U.S. Air Force patrol dog training school in Weisbaden, West Germany. In January of 1971, recurrence of the gastroenteritis disease syndrome was observed and the causative agent was identified as a CCV. In 1972 Cartwright and Lucas reported that antibody titers to transmissible gastroenteritis (TGE) virus had significantly increased in dogs after an outbreak of vomiting and diarrhea. It was concluded that TGE or more probably a serologically related virus such as CCV produced disease in these dogs.

Infection results from contact between infected and susceptible dogs. Infected dogs usually show symptoms of disease. However, dogs recovering from disease may shed virus in their feces and prove to be a continued source of infection for susceptible dogs.

In 1978 with the sudden outbreaks of Canine Parvo virus-induced enteritis, a renewed vigor and interest in canine enteric viruses was stimulated. First efforts were directed toward finding the causative agent for this new hemorrhagic enteritis-myocarditis syndrome which was severe and most often fatal. Upon investigation researchers discovered two distinct viruses, Canine Corona Virus (CCV) and Canine Parvo Virus (CPV). After further investigation the CPV proved to be the new agent, most often causing the highest morbidity and mortality. The CCV induced a disease somewhat similar but less often fatal. The simultaneous isolation of CPV and CCV has been reported. One survey that was conducted indicated that 17% of the cases of canine enteritis were found to be dual infections with CPV and CCV. Various state diagnostic laboratories confirm these findings.

Differentiation of Parvoviral and Coronaviral enteritis is difficult. The probable simultaneous infections with both viruses makes differentation even more difficult. In a serological survey in a kennel situation, 55% of the dogs tested were found to have been exposed to both CCV and CPV. Some kennels tested had up to 87% positive exposure to both agents. The severity of the enteritis attributable to simultaneous infection is unknown. However, one expert researcher in the field proposes that infection by both viruses increases the probability of morbidity in the dog.

As noted above, CCV enteritis is a highly contagious disease which has been observed on a world-wide basis. The incidence of CCV disease in family-owned dogs has been reported to range from 14.8% to 26%. The incidence in kennel-raised dogs ranges upwards to 30%. The incidence of gastroenteritis where both CCV and CPV were isolated is even higher. The disease can occur in dogs of any age. The importance of CCV gastroenteritis has seemingly increased with the outbreak of CPV gastroenteritis.

CCV gastroenteritis is characterized by a number of disease symptoms which have been compiled from the literature as follows: the first signs of disease are lethargy, anorexia and depression. The sudden onset of vomiting occurs in which blood can sometimes be found. Diarrhea can range from moderate to severe and projectile in nature. Diarrhea may persist for up to 10 days. The fecal material has a yellow-orange color with blood and mucus occasionally found therein. Moreover, the fecal material has a marked foul odor. The intestinal tract will contain watery, yellow-green material. Dehydration, weight loss and death have been reported. Protracted or recurring diarrhea may occur 2–3 weeks later. The severity of the CCV disease syndrome is thought to vary according to age, stress, environmental conditions, breed and concurrent infections. CCV has also been associated with respiratory disease symptoms of ocular and nasal discharge.

Both respiratory and enteric symptoms of disease have been seen experimentally by the present inventors. The symptoms observed have included a slight ocular discharge, a slight nasal discharge, diarrhea, weight losses, anorexia, dehydration, elevated temperatures and slight drops in both white blood cell levels and lymphocyte levels. Intestinal samples of infected dogs demonstrated that a significant degree of virus infection occurs following challenge.

CCV is a member of the Corona Virus group of viruses. Some pertinent characteristics of the Corona Virus group include:

(a) The virus particle is spherical or elliptical with knoblike projections on the outer surface of 18–20 nanometers (nm).

(b) The viruses have very fastidious in vitro growth requirements.

(c) The virus particle sizes vary in diameter from 80–200 nm.

(d) The virus has a single stranded RNA nucleoprotein.

(e) The virus develops in the cytoplasma of the cell.

(f) There is a complex antigenic similarity within the group.

(g) The virus density in cesium chloride (CsCl) is 1.24 to 1.26 g/ml.

Studies show that there do not appear to be distinct antigenic differences among various CCV isolates.

The veterinary community has recognized the need for a CCV vaccine but the literature indicates that little successful work has been done in this area. Experts in the field have recommended an oral-intranasal route of vaccination to insure not only the achievement of systemic immunity but also the obtention of local immunity in the intestinal tract.

SUMMARY OF THE INVENTION

The present invention is directed to a new attenuated Canine Corona virus, a new method for attenuating Canine Corona virus, a new Canine Corona virus vaccine composition, a new method for propagating Canine Corona virus, a new method for vaccinating dogs and a new method for evaluating the effectiveness of a Canine Corona virus vaccine.

The Canine Coronavirus composition of this invention comprises attenuated modified live or killed Canine Coronavirus in an amount effective to protect a dog from infection by virulent Canine Coronavirus and a non-toxic pharmaceutically acceptable carrier or diluent. The invention in another aspect relates to a method for protecting dogs from infection caused by Canine Corona virus, comprising administering to a dog a vaccine composition containing an attenuated modified live or killed Canine Corona virus in an amount sufficient to protect said dog from infection by virulent Canine Corona virus.

The original isolation of the virulent CCV was made from a dog which died of gastroenteritis. The isolate was given the designation TN-449. Virus detection methods including electron microscopy indicated CCV as the only virus present in the specimens taken from the dog. This virus isolate was then placed in CRFK cell cultures for propogation and attenuation purposes. A low virus inoculum was placed in CRFK cell cultures which became confluent in 24 hours or less. A virus to cell ratio of about 1 to 3,000 was utilized. The low virus input requires an increased number of virus multiplications which aids in the attenuation process. The virus passaging took about two months. Twelve consecutive cell passages were performed in a heterologous cell culture such as CRFK to achieve attenuation. Dogs were inoculated with various dose levels of passage 12 material. Dose levels of 7.5 $\log_{10}$, 5.5 $\log_{10}$, 3.5 $\log_{10}$ and 1.5 $\log_{10}$ were used parenterally in dogs. A non-inoculated dog was held as a contact control dog. These animals were observed following vaccination. The dogs remained healthy with no symptoms of gastroenteritis being observed. Post inoculation serology verify the virus inoculum had replicated in the dogs. This demonstrated the attenuation of the TN-449 virus. An additional virus passage of the TN-449 was made to establish the Master Seed Virus. The TN-449 culture has been deposited with the American Type Culture Collection in Rockville, Md. and has been given ATCC Deposit No. VR 2068.

The new attenuated modified live Canine Corona Virus has three distinguishing characteristics which make it very useful as a vaccine virus (1) the attenuated CCV is fully adapted to growth and reproduction in cell culture, especially cells of feline or canine origin, (2) the attenuated CCV does not produce disease when administered to a dog and (3) when administered by injection, e.g. subcutaneously, parenterally, etc., the virus selectively infects intestinal epithelium. Because of these unique characteristics of the attenuated CCV localized immunity in the intestines is produced when the virus is administered to dogs.

These unique characteristics appear to be due to the method used to attenuate the virus. Modified attenuated live CCV suitable for use in the present invention is prepared by passing a virulent CCV strain in cells of feline origin at least eight times at a low virus to cell ratio of 1:1,000–10,000, preferably 1:1,500–7,500 wherein the virus particles are measured by the $TCID_{50}$ method (Tissue Culture Infective Dose).

Passing the virus at a low virus to cell ratio speeds up attenuation and allows the cells to become attenuated with a minimum number of passages. The low virus to cell ratio also acts to genetically select only those cells which are fully adapted to cell culture, thereby producing an attenuated virus strain which is useful for use in a vaccine. For attenuation purposes, feline cells should be used and canine cells should be avoided. The CCV appears to become attenuated easily in feline cells, however, if canine cells are used a possibility exists that the virus would revert back to the virulent state. Thus, when the attenuated CCV is grown for production purposes, more than one or two passages in canine cells should be avoided. The cells should be passed through the feline cells at least eight times usually 8 to 60 passages and preferably 8 to 25 passages.

The CCV vaccine composition includes an attenuated modified live virus having a titer of greater than 2.5 $\log_{10}$ of virus particles/ml (or dose) preferably at least 3.0 logs of virus particles/ml (or dose) and more preferably greater than 3.3 logs of virus particles/ml (or dose) as measured by the $FAID_{50}$ (Fluorescent Antibody Infectious Dose) method (King et al, Can. Journal of Comparative Medicine & Vet. Science, 29, pp. 85–89 (1965)). Titers as high as 5 to 7 logs $FAID_{50}$ have been obtained. The CCV vaccine composition includes an attenuated modified live CCV and also may contain an attenuated modified live CPV or killed virus. In addition, the vaccine may contain additional attenuated modified live virus or killed viruses such as Canine Distemper virus, Canine Parainfluenza virus, Canine Adenovirus I, Canine Adenovirus II and Canine Rotavirus. The attenuated modified live CCV virus produces a complete immunological response to the virus infection. However, the infection produces a fever about 0.5° to 1.0° F. lower than the virulent strain of CCV. The vaccine composition contains a sufficient amount of the attenuated modified live virus to produce an immunological response in a dog and a non-toxic pharmaceutically acceptable sterile carrier or diluent such as a sterile saline solution. Preferably the carrier or diluent is suitable for parenteral injection, however, the carrier or diluent may also be of a type which is suitable for use as a nasal spray.

The method for propagating the CCV in mammalian cells includes the steps of inoculating mammalian tissue culture cells with CCV, cultivating the cells into a one hundred percent (100%) confluent tight monolayer before said inoculating step or within 24 hours of said inoculating step, harvesting the cells between 24 and 96 hours after inoculation and collecting the propagated virus from the harvested cells.

The mammalian tissue culture cells are inoculated with CCV at a CCV virus (measured by the $FAID_{50}$ method) to cell ratio of 1:500 to 1:1, preferably 1:100 to 1:5, more preferably 1:75 to 1:10. The mammalian tissue culture cells include but are not limited to Crandall Feline Kidney Cells (CRFK), Wood's Feline Cell Line (FC), a Dog Kidney Cell Line (DK), Madin Darby Canine Kidney (MDCK) and the canine A72 cell line. The CCV is added to a suspension of the cells or is applied to a monolayer of the cells. The amount of cells and virus should be such that a confluent tight monolayer of the cells will form wiithin 12–48, preferably 24–36, hours after inoculation. Optimally, at the time of inoculation the cells should be present in the growth vessel in an amount sufficient to form a monolayer of cells of at least 100,000 cells per square centimeter ($cm^2$) within about 12–48 hours after inoculation, preferably within 24 hours after inoculation. However, a lesser number of cells may be used. The cells should be present in an amount sufficient to form a monolayer of cells of less than 1,000,000 cells/$cm^2$ within 12–48 hours, preferably within 24 hours. Preferably the cells are present in an amount sufficient to form between 150,000 to 500,000 cells/$cm^2$ within 12–48 hours, preferably within 24 hours. The virus is adsorbed on the cells for at least 60 minutes but usually less than 300 minutes, preferably between 90 and 240 minutes at 28° to 40° C., preferably 35° to 38° C.

Harvestable virus titers of at least about 1,000 and usually at least about 2,000 as measured by the $FAID_{50}$ method can be obtained within 18 hours after inoculation, however, in some circumstances it may take up to 120 hours or longer to obtain maximum virus titers. Maximum virus titers are usually obtained within about 24 to 96 hours after inoculation. The cell monolayer is removed either by freeze-thawing or by enzymatic action to increase the viral content of the harvested fluids. The harvested fluids are then either combined with a virus stabilizer such as sucrose phosphate glutamate (SPG), sucrose phosphate glutamate albumin (SPGA) or NZ amine-gelatin for final product filling or frozen in bulk for later thawing and bulking with virus stabilizer.

A further aspect of the invention concerns the route of administration. The induction of humoral-systemic protection as measured by serum neutralizing antibody levels as well as the induction of local immunity in the intestinal tract is an important feature of this invention. The oral-intranasal routes of administration should elicit both types of protection, however, the general marketplace acceptance of this route of administration is not good and, therefore, the use and subsequent protection afforded by a CCV vaccine would not be realized. Therefore, one major aspect of this invention is the parenteral vaccination of a CCV vaccine which induces both humoral immunity and localized immunity. The term parenteral vaccination is intended to include subcutaneous and intramuscular inoculation routes.

The vaccine is usually parenternally administered in a dose of at least 2.5 logs of virus particles per dose, preferably at least 1,000 virus particles (3 logs of virus particles) per dose, more preferably at least 3.3 logs of virus particles per dose.

Another aspect of the present invention is the method utilized to evaluate the effectiveness of a CCV vaccine. The method includes the steps of vaccinating a dog with an attenuated modified live CCV vaccine, bleeding the vaccinated dog after the dog has developed an immunological response to the vaccine, separating the serum from the blood, challenging the vaccinated test dog and a non-vaccinated dog with an infectious amount of a virulent CCV by an intranasal-oral route, and examining intestinal tract samples of the vaccinated dogs and the control dogs to determine the degree of replication of the challenge virus. The United States Department of Agriculture (USDA) has standard testing requirements for determining the host animal effectiveness of some veterinary products. No standard requirement, nor proposed testing requirements, are in existence for CCV vaccines. Furthermore, no adaptations of standard or proposed testing procedures were possible to validly evaluate the effectiveness of the product in host animals. Therefore, a new test method for evaluating the effectiveness of the CCV vaccines has been developed. This procedure involves the direct measure of protection afforded in the intestinal tract of vaccinated animals against infection of the intestinal tract with virulent Canine Corona challenge virus. In general, vaccinated dogs are bled at least seven and preferably 7 to 21 days following vaccination to determine the humoral protection afforded by measuring the quantity of serum-neutralizing antibody present in the serum. These dogs, along with nonvaccinated control dogs, are then challenged with virulent CCV by the intranasal-oral route. The intestinal tract samples of both vaccinated and control dogs are examined to determine the degree of challenge virus replication which has taken place. Sampling can be performed between 2 and 14, preferably between 3 and 10 days after challenge. Direct impression smears, intestinal scrapings, or processed intestinal scrapings can be used for evaluation purposes.

The detection of virus in the intestinal sample includes but is not limited to both direct and indirect fluoroscent antibody staining. The measure of vaccine effectiveness for providing local immunity is measured by the difference in the degree of infection between vaccinated and control dogs. A reduction in infection of 90% is not unusual.

DETAILED DESCRIPTION OF THE INVENTION

The present invention is based upon several discoveries. One discovery is the method of propagation used for the Canine Corona Virus which yields sufficiently high titers for blending purposes as required in vaccine preparation. The propagation of Canine Corona Virus to high virus infectivity levels can be difficult so that this aspect of the invention is extremely important. The methods of production developed yield virus infectivity titers of at least 3 logs of virus per ml as measured by the direct $FAID_{50}$ method.

A further point to be noted in connection with this aspect of the invention is that the CCV titers achieved by the method described herein are sufficient to blend with virus stabilizer components but also of sufficient quantity to allow for the combining of CCV with other virus agents such as but not limited to Canine Parvo Virus, Canine Distemper virus, Canine Adenovirus I, Canine Adenovirus II, Canine Parainfluenza, Canine Rotavirus, *Leptospira canicola* and *Leptospira icterohaemorrhagiae*.

Some major factors in achieving high titer Corona virus are the virus cell ratio adsorption time of virus and cells, cell contact inhibition obtained, and the harvest time of virus fluids following inoculation.

A modified live CCV is used in conjunction with either primary cell cultures or an established cell line of either canine or feline origin. Incubation temperatures of 28°–40° C. are employed with 35° to 38° being preferred. An MEM-Earles tissue culture media supplemented with an animal serum such as bovine is used. A minimum concentration of 5–10% is used for cell culture growth and a concentration of not less than 1% is used in the maintenance medium. A minimum concentration of 0.5 ml of an enzyme such as crude or purified trypsin per liter of tissue culture medium is used. Cell cultures are planted in either stationary or roller culture bottles.

In the case of cell monolayers, a cell population of not less than 150,000 cells per square centimeter is used. The monolayer appears tight and confluent, thereby giving the contact cell inhibition needed. The cell culture growth media is removed and seed virus is added. Frozen CCV seed is thawed in cold water and placed in at least a sufficient volume (such as 50 ml) on the cell monolayer for an adsorption period of at least 90 minutes at temperatures between 35° and 38° C. A minimum virus to cell ratio of 1 virus particle to every 100 cells is essential.

In the case of a cell suspension, sufficient cells are used per a specific surface area to ensure that a crowded, confluent monolayer is obtained in 24 hours or less. A cell culture passage of 1 vessel of uninoculated cells to 1 or 2 vessels for infected cells may be used.

The time of harvest is critical in obtaining sufficient titers of CCV for vaccine blending. An infectivity titer of at least 3.3 logs of virus per ml is needed. The harvest times required to obtain virus titers of this magnitude range from 24 hours after infecting the cell population to 96 hours after cell population infection. Virus infectivity titers peak at 48 hours and decline thereafter. However, sufficient infective virus will remain up to about 96 hours. Virus infectivity titers can be increased by at least two fold by removing the remaining cell monolayer by enzymatic action or by freeze-thawing and adding the cell suspension to the previously harvested virus fluids.

Another major discovery of this invention is that the vaccine virus will provide humoral, systemic protection as measured by serum neutralizing antibody levels and localized intestinal protection as measured by vaccination-challenge studies when the vaccine is administered parenterally. Unexpectedly, it was found that induction of localized immunity has been associated with routes of vaccination other than parenteral and the possibility of providing local immunity to the intestinal tract by parenteral vaccination with CCV was deemed unlikely. The systemic immunity is likely due primarily to the presence of gamma-immunoglobulin (IgG) and the local immunity in the intestinal tract is likely due at least partially to the presence of alpha-immunoglobulin (IgA) as well as IgG.

Experimentation with various dosage levels of CCV vaccine given by the parenteral route of vaccination demonstrated vaccine viral replication in the intestinal tract as early as five days after administration and a serological response as early as 7 days after administration. Vaccinated dogs, when challenged, indicated a reduction of disease symptoms and up to a 95% reduction in intestinal infection as compared to unvaccinated controls. The data thus supports the uniqueness of this portion of the discovery that parenterally administered CCV vaccine provides systemic, humoral protection as well as local immunity in the intestinal tract.

Another discovery of this invention comprises the means by which the vaccine is evaluated in canines. The vaccine is designed to prevent systemic and localized gastroenteritis infections induced by the CCV. Circulating or humoral antibody evaluations were conducted on blood samples taken 7 to 21 days after parenteral vaccination with 2.9 $FAID_{50}$ logs of vaccine virus per dog. At 21 days after vaccination, vaccinated dogs and non-vaccinated dogs were intranasally-orally challenged with virulent Canine Corona Virus. The onset of disease is rapid and sudden. Disease symptoms are seen as early as 24 hours after challenge in susceptible dogs. The duration of symptoms is usually 24-96 hours, but can extend to 10 days. In evaluating the effectiveness of the vaccine, the animals are euthanized at 5, 6, or 7 days after challenge. The intestinal tract from the pyloric valve to the large intestines is removed. The intestines are processed (see Example 5) and examined by impression smear scrapings or exfoliated intestinal epithelium is used (Example 5).

The impression smears are made by scraping the epithelial lining systematically at several locations throughout the intestine. The scrapings are put on slides and processed for direct fluorescent antibody staining to detect CCV infected cells. The same epithelial scrapings may be exfoliated by placing the scrapings in phosphate buffered saline. The epithelium saline mixture is agitated to suspend the individual cells in the saline. Then, samples of the suspensions are placed on slides to be processed for direct fluorescent antibody (FA) staining for CCV.

The examination of the slides reveals the extent of specific fluorescence as a measure of virus infection. The degree of fluorescence based on the number of infected cells per field in conjunction with the number of samples examined per dog yield a numerical value of infection which can be assigned to each individual animal. Thus, evaluation as to degree or extent of CCV infection in the intestinal tract is obtained. Comparison of the values from vaccinated and non-vaccinated dogs yields a means of evaluating the effectiveness of the vaccine in preventing intestinal infection (see Example 5).

EXAMPLE 1

VACCINE PRODUCTION

The production strain was originally isolated from a dog which had died of CCV enteritis. The virus was serially propagated in Crandal Feline Kidney Tissue (CRFK) culture. Upon receipt the virus labeled TN-449 was designated CCV-MSV and passaged once to Master Seed CCV-MSV(X). The CCV-MSV (Canine Corona Virus-Master Seed Virus) TN-449 culture has been deposited with the American Type Culture Collection in Rockville, Md. and given ATCC Deposit No. VR 2068. Other attenuated modified live CCV might also be used instead of the CCV-MSV. The virus is commonly grown in CRFK cultures. The cell cultures are grown in dynamic cultures. In some preliminary runs, static cultures were used. Cell cultures are grown in minimal essential media (MEM) supplemented with vitamins, non-essential amino acids, sodium pyruvate, $NaHCO_3$ and L-glutamine. 30 mcg/ml of gentamicin is added as a preservative. A 5-10% concentration of bovine serum is added for cell growth. The serum concentration is reduced to 1% for a maintenance medium. Trypsin is added at a concentration of 0.5 ml/liter of medium to promote virus infectivity.

Confluent cultures of CRFK cells are trypsinized and planted into roller cultures so that a density of 150,000 cells per $cm^2$ may be obtained after 24 hours. Cultures are grown at 28° to 40° C., preferably 35°-38° C. The growth media is removed.

The production seed virus is thawed in cool running water. Sufficient virus is added to achieve a minimum multiplicity of infection (MOI) ratio of 1:100. A 2000 $cm^2$ bottle contains 300-500 million cells. At a 1:50 MOI $300 \times 10^6$ divided by 50 yields a minimal infective virus inoculum of $6 \times 10^6$ or $10^{6.8}$ $FAID_{50}$ per roller. Virus seeds and product harvests yield $10^{5.5}$ to $10^{7.0}$ $FAID_{50}$ per ml. Thus 20 ml of undiluted to 1 ml of undiluted seed is usually used per bottle. The seed is brought up to a volume of 50 ml per roller bottle with culture medium. The virus is allowed to adsorb on monolayers or in suspension for 2 hours at 35° to 38° C. A specific example uses a seed titered at $10^{5.7}$ $FAID_{50}$ per ml with 15 ml per roller used as the inoculum. Thirty two roller bottles were inoculated as described. The bottles were refed with 2 liters of MEM at 1% FCS and 0.5 ml of trypsin. The fluids were harvested along with the cellular material 48 hours after infection, dispensed and frozen at $-40°$ C. or lower.

The bottles yielded 66.5 liters of virus fluids. The titer of the fluids was $10^{5.0}$ $FAID_{50s}$ per ml. The material was later thawed and blended with media and SPGA (Sucrose Phosphate Glutamate Albumin) stabilizer and lyophilized.

EXAMPLE 2

INTESTINAL PROPAGATION THROUGH PARENTERAL INOCULATION

The purpose of the study was to determine whether the Canine Corona Vaccine Virus would locate and replicate in the intestinal tract when administered intranasally or intramuscularly to healthy susceptible dogs.

Four dogs were divided into two groups, isolated, and bled prior to vaccination. Dogs Nos. 63 and 64 were vaccinated intramuscularly with a 10 ml dose ($10^{6.3}$ $FAID_{50}$/dose) of CCV (x+1) seed (seed prepared by one additional passage from the master seed). The two other dogs Nos. 62 and 65 were vaccinated intranasally with a 2 ml dose ($10^{5.6}$ $FAID_{50}$/dose) of the same CCV seed. On day 5 after vaccination the dogs were bled, swabbed for fecal samples for virus isolation in CRFK cell culture, and euthanized. Tissue scrapings from the trachea, duodenum, jejunum and cecum were placed on slides. These impression smears were then subjected to observation for virus replication by the direct fluorescent antibody technique.

Fecal Virus Isolation

No Corona virus could be isolated from the feces.

Direct FA Staining of Impression Slides

The results of fluorescent antibody staining of tissue impression slides are shown in Table 1.

TABLE 1

| | | | CCV Direct FA of Impression Slides | | | | | |
|---|---|---|---|---|---|---|---|---|
| Dog No. | Virus Input ($FAID_{50}$/dose) | Vaccination Route | CCV+ slides/No. of slides taken: Trachea | Duodenum | Jejunum | Cecum | CCV+ Total slides/slides TOTAL | CCV Positive (%) |
| 63 | $10^{6.3}$ | IM | NA | 10/12 | 4/7 | 3/5 | 17/24 | 71 |
| 64 | $10^{6.3}$ | IM | NA | 3/6 | 4/5 | 4/5 | 11/16 | 69 |
| 62 | $10^{5.7}$ | IN | 3/4 | 2/2 | 2/2 | 2/2 | 6/6 | 100 |
| 65 | $10^{5.7}$ | IN | 2/2 | 2/2 | 4/4 | 5/5 | 11/11 | 100 |

One hundred percent of the intestinal impression slides taken from the intranasally inoculated dogs were positive for virus replication, while seventy percent of the intestinal impression slides were positive for virus replication from the dogs inoculated intramuscularly.

Virus replication occurred in all three sections of the intestinal tract. Virus replication was also observed in the trachea of the dogs vaccinated intranasally.

The degree of virus involvement in the intestine of intranasally inoculated animals and the fact that the trachea also exhibited virus replication may indicate this route of inoculation as the natural portal of entry for infection.

Conclusion

Virus replication in the intestinal tract can be achieved 5 days after administering high dose levels of virus either intramuscularly or intranasally.

EXAMPLE 3

LOW VIRUS INOCULUM PARENTERALLY ADMINISTERED FOR INTESTINAL REPLICATION

The purpose of this study was to determine whether the CCV vaccine when administered intramuscularly in a low dose level would locate and replicate in the intestinal tract.

Two dogs Nos. 60 and 68 were vaccinated intramuscularly with 1 ml of the CCV-MSV (x+3) seed diluted to $10^{3.0}$ $FAID_{50}$/ml. On day 5 after vaccination the dogs were bled and euthanized. Impression smears from villi scrapings were made from the duodenum, jejunum and cecum for direct FA observation to detect virus replication. These smears were processed and stained with CCV specific FITC (fluoroisothiocyanate) bound conjugate and examined via FA.

Direct CCV FA from Villi Scrapings

Recovery of positive CCV from the villi scraping slides are shown in Table 2.

TABLE 2

| | | | CCV Direct FA of Villi | | | | |
|---|---|---|---|---|---|---|---|
| Dog No. | Virus Input | Vaccination Route | CCV + Slides/ No. of Slides Taken: Duodenum | Jejunum | Cecum | CCV + Total Slides/ Slides TOTAL | Positive (%) |
| 60 | $10^{3.0}$ | IM | 6/7 | 5/7 | 6/6 | 17/20 | 85 |
| 68 | $10^{3.0}$ | IM | 4/6 | 5/6 | 4/6 | 13/18 | 72 |
| | | | | | | | Avg. % = 79 |

CCV replication was found in all areas of the intestinal tract of both dogs 5 days following the intramuscular administration of 3 logs of virus. An average of 79% of the samples observed were positive for virus replication. This percentage compares favorably with the 70% positive sample obtained with dogs administered with 5.6 logs of virus in another study.

CCV replication can be demonstrated in the intestinal tract of susceptible dogs vaccinated parenterally with $10^{3.0}$ $FAID_{50}$/dose of CCV vaccine 5 days after vaccination.

EXAMPLE 4

PRELIMINARY VACCINE AND CHALLENGE EVALUATION

The purpose of this study was to evaluate a Canine Corona Challenge Virus and to determine if the vaccine virus will prevent any symptoms induced by the challenge virus and reduce or prevent intestinal infection by the challenge virus.

Two Canine Corona virus-susceptible dogs, Nos. 61 and 66, were bled and vaccinated intramuscularly with 3 logs of CCV MSV (x+3) seed. These animals were held in isolation until the time of challenge.

At 21 days after vaccination the two CCV vaccinates along with the four CCV susceptible dogs Nos. 75, 79, 74 and 76 were bled, anesthetized and challenged with 5 ml/dog of CCV challenge virus. Each dog received 2 ml orally and 3 ml intranasally. Each dog received $10^{5.7}$ $FAID_{50}$ of challenge virus.

Dogs Nos. 74 and 76 were monitored for 7 days after challenge for temperature response, WBC (white blood cell) count, lymphocyte count response and other symptoms. At 5 days after challenge the two CCV vaccinates Nos. 61 and 66 along with the two challenge control dogs Nos. 75 and 79 were euthanized. Intestinal scraping impression smears were made of the duodenum, jejunum and cecum of each dog. Fluorescent antibody staining was performed on these smears to determine the extent of viral replication in the intestinal tract.

TABLE 3

CCV SN Testing

| Dog No. | Group | CCV Serum Neutralizing (SN) Antibody Titer | |
|---|---|---|---|
| | | Pre-vaccination | Pre-Challenge |
| 61 | V* | <1:2 | 1:1122 |
| 66 | V | <1:2 | 1:1122 |
| 75 | C** | | <1:2 |
| 79 | C | | <1:2 |
| 74 | C | | <1:2 |
| 76 | C | | <1:2 |

*Vaccinate
**Challenge Control

Both vaccinates were seronegative prior to vaccination and seroconverted to a 1:1122 level 21 days after vaccination.

An average of 95.6 percent of all intestinal samples observed in the controls demonstrated a 4(+) virus replication level. None of the vaccinates demonstrated a 4(+) level of virus infection in the intestinal samples. Therefore a 100% reduction in the 4(+) level of infection was achieved.

A total of 17.4 percent of the vaccinate samples were positive with a 1(+) level of infection whereas a total of 100% of the challenge control samples were positive (95.6% at 4+, 4.4% at 1+). An overall percent reduction in intestinal infection of 82.6% was achieved in the vaccinates.

Further analysis of this data can be performed which gives significance to the 4+ level of infection in comparison with a 1+ level of infection. This analysis can be found in Table 4.

TABLE 4

| Dog No. | Degree of Infection | Number of Intestinal samples (+) per group | Number of samples multiplied by the degree of infection | Total Number per group of Infective Index |
|---|---|---|---|---|
| Controls | | | | |
| 75 | 4+ | 22 | 88 | 178 |
| | 1+ | 1 | 1 | |
| | 0 | 0 | 0 | |
| 79 | 4+ | 22 | 88 | |
| | 1+ | 1 | 1 | |
| | 0 | 0 | 0 | |
| Vaccinates | | | | |
| 61 | 4+ | 0 | 0 | 8 |
| | 1+ | 7 | 7 | |
| | 0 | 16 | 0 | |
| 66 | 4+ | 0 | 0 | |
| | 1+ | 1 | 1 | |
| | 0 | 22 | 0 | |

CCV Challenge Evaluation Results and Discussion

1. Temperature Response
Post CCV Challenge Temperature Response (100° F.)

| Dog No. | Group | Day Post Challenge | | | | | | |
|---|---|---|---|---|---|---|---|---|
| | | 0 | 1 | 3 | 4 | 5 | 6 | 7 |
| 74 | Monitored challenge control | 2.2 | 2.5 | 3.6* | 4.4 | 2.8 | 2.0 | 2.0 |
| 76 | Monitored challenge control | 2.0 | 2.2 | 4.0* | 4.2 | 3.2 | 2.6 | 2.0 |
| AVG. | | 2.1 | 2.4 | 3.8 | 4.3 | 3.0 | 2.3 | 2.0 |
| 75 | Euthanized challenge control | Not taken until severe temp noted in Nos. 74 & 76 | | 3.0 | 4.0* | 3.5* | Euthanized for Gut FA | |
| 79 | Euthanized challenge control | Not taken until severe temp noted in Nos. 74 & 76 | | 4.6* | 4.0* | 3.4 | Euthanized for Gut FA | |
| AVG. | | | | 3.8 | 4.2 | 3.2 | | |
| 61 | CCV vaccinate | Not taken until severe temp noted in Nos. 74 & 76 | | 2.2 | 2.0 | 1.6 | Euthanized for Gut FA | |
| 66 | CCV vaccinate | Not taken until severe temp noted in Nos. 74 & 76 | | 2.6 | 3.0 | 2.6 | Euthanized for Gut FA | |
| AVG. | | | | 2.4 | 2.5 | 2.0 | | |

*critically high fever

The CCV challenge produced a critically high fever (103.5° F.) in the CCV susceptible challenge control dogs for days 3, 4, 5 respectively. All of the four challenge control dogs expressed temperatures of 103.5° F. for two consecutive days. Dogs 74 and 76 averaged temperature of 103.8° F. and 104.3° F. on day 3 after challenge and 104° F. on day 4 after challenge. Dog 75 had a delayed temperature response of 104° F. and 103.5° F. on days 4 and 5 after challenge.

The CCV vaccinated dogs displayed no temperature over 103° F. for the 3 days they were monitored during the critical fever period. The CCV challenge produced a significant febrile response in CCV susceptible dogs and the CCV vaccine prevented this temperature increase.

2. WBC Response

| | Days Post Challenge | | | | | | |
|---|---|---|---|---|---|---|---|
| Dog No. | 0 | 1 | 3 | 4 | 5 | 6 | 7 |
| | WBC Count Post CCV Challenge (X100) | | | | | | |
| 74 | 195 | 252 | 178* | 125* | 125* | 134 | 169 |
| 76 | 247 | 177 | 130* | 85* | 105* | 155 | 150 |
| | Percentage WBC Drop Post CCV Challenge | | | | | | |
| 74 | 0 | — | 8.7 | 35.9 | 35.9 | 31.3 | 13.3 |
| 76 | 28 | — | 47 | 65.6 | 57.5 | 37.2 | 39.3 |

*critical days

The critical period for a WBC drop following CCV challenge was on days 3, 4 and 5. This data indicates WBC monitoring may be a critical parameter for the Canine Corona virus disease syndrome.

3. Lymphocyte Count
Lymphocyte Count Post CCV Challenge (X100)

| Dog No. | Days Post Challenge | | | | | |
|---|---|---|---|---|---|---|
| | 0 | 1 | 3 | 4 | 5 | 6 | 7 |
| 74 | 82 | 103 | 43* | 39* | 31* | 56 | 61 |
| 76 | 131 | 58* | 46* | 29* | 29* | 68 | 65 |

*critical days

A lymphopenia developed in the CCV challenge control dogs beginning on day 1 with dog 76 and day 3 with dog 74. The lymophopenia continued through day 5 after challenge. Further analysis of the percent lymphocyte drop is listed below:

Percentage Lymphocyte Drop Post CCV Challenge

| Dog. No. | Days Post Challenge | | | | | |
|---|---|---|---|---|---|---|
| | 1 | 3 | 4 | 5 | 6 | 7 |
| 74 | — | 48 | 52* | 62* | 32 | 26 |
| 76 | 36* | 65* | 78* | 78* | 48 | 50 |

*critical days

Lymphopenia with over a 50% reduction in lymphocytes occurred in 6 of 12 observations of the challenge control dogs with the most severe occurrences on days 4 and 5 after challenge. Dog 74 had greater than 50% lymphopenia on days 4 and 5 after challenge. Dog 76 displayed a lymphopenia over 50% on days 3, 4, 5 and 7 after challenge and had the largest drop of 78% on days 4 and 5 after challenge.

4. Symptoms
Symptoms Post CCV Challenge

| Dog No. | Days Post Challenge | | | | | | |
|---|---|---|---|---|---|---|---|
| | 0 | 1 | 3 | 4 | 5 | 6 | 7 |
| 74 | None | None | Nasal Discharge Anorexia Dehydration Feces Dry | Slight Nasal Discharge Slight Ocular Discharge Anorexia Dehydration Feces Wet | Soft Stool | Slight Nasal Discharge | Slight Nasal and Ocular Discharge |
| 76 | None | None | Nasal Discharge Anorexia Dehydration Feces Dry | Slight Nasal Discharge Slight Ocular Discharge Anorexia Dehydration Feces Wet | Slight Nasal Discharge Feces Soft | Slight Nasal Discharge | Slight Nasal and Ocular Discharge |

Symptoms of CCV infection began on day 3 after challenge and ran concurrent with the febrile response and lymphopenia. Symptoms of nasal discharge, anorexia, dehydration, and ocular discharge continued through day 7 after challenge, the last day of monitoring. The CCV challenge produced significant CCV symptoms in CCV susceptible dogs.

Evaluation of Virus Replication in the Intestinal Tract of Vaccinates and Controls 5 Days After Challenge A total of 8 locations were selected in the trachea for impression slide preparations and 23 locations were selected along the intestinal tract for evaluation. Intestinal scrapings were placed on slides which were acetone fixed and stained with specific Canine Corona virus FA conjugate. The degree of replication was evaluated as to a 4+ infection, 1+ infection or no virus present. The results of these evaluations are shown in Tables 5 and 6.

TABLE 5
Sample Evaluation For Canine Corona virus Replication

| Group | Dog No. | Degree of FA+ | No. of Slides | | | | |
|---|---|---|---|---|---|---|---|
| | | | Trachea | Duodenum | Jejenum | Cecum | TOTAL |
| Challenge control | 75 | 4+ | 0 | 6 | 8 | 8 | 22 |
| | | 1+ | 0 | 1 | 0 | 0 | 1 |
| | | No CCV | 8 | 0 | 0 | 0 | 8 |
| Challenge control | 79 | 4+ | 0 | 6 | 8 | 8 | 22 |
| | | 1+ | 0 | 1 | 0 | 0 | 1 |
| | | No CCV | 8 | 0 | 0 | 0 | 8 |
| Vaccinate | 61 | 4+ | 0 | 0 | 0 | 0 | 0 |
| | | 1+ | 0 | 2 | 4 | 1 | 7 |
| | | No CCV | 8 | 5 | 4 | 7 | 24 |
| Vaccinate | 66 | 4+ | 0 | 0 | 0 | 0 | 0 |
| | | 1+ | 0 | 0 | 0 | 1 | 1 |
| | | No CCV | 8 | 7 | 8 | 7 | 30 |

No Trachea virus replication was noted in any of the dogs. Further evaluation of the percent of positive samples will exclude the trachea samples.

TABLE 6

| Dogs | Percent of samples FA(+) per degree of infection in the intestinal tract | | | Average Total Percent per test group | |
|---|---|---|---|---|---|
| | 4+ | 1+ | 0 | (+) | (−) |
| 75 | 95.6 | 4.4 | 0 | | |
| 79 | 95.6 | 4.4 | 0 | | |
| Control Average | 95.6 | 4.4 | 0 | 100 | 0 |
| 61 | 0 | 30.4 | 69.6 | | |
| 66 | 0 | 4.4 | 95.6% | | |
| Vaccinate Average | 0 | 17.4 | 82.4 | 17.4 | 82.4 |

An infective index level of 178 for the controls versus 8 from the vaccinates indicates a reduction in infection of 95.5%.

The study thus establishes that the CCV challenge produced severe measurable clinical symptoms of CCV disease and the CCV challenge can be observed in the gut. The CCV vaccine lowers the degree of infection in the vaccinated dog's gut and eliminates the clinical symptoms and fever after CCV challenge when compared with CCV susceptible challenge control dogs.

EXAMPLE 5

VACCINE EFFICACY

Pups were proven seronegative to CCV by a serum neutralization test via F.A. Twenty-two of the animals were vaccinated with a minimal dose of vaccine. One half of the group was given the vaccine subcutaneously and the other half of the group was administered vaccine intramuscularly. The vaccinated dogs then were housed individually but kept in the same area along with three more pups, which served as environmental controls. The animals were monitored and held for three weeks. No untoward effects from the vaccine were displayed and there were no signs of environmental exposure to virus.

Each vaccinate was housed so as to prevent direct dog to dog contact. This procedure was employed to prevent a vaccinate, which may be shedding, from inadvertently exposing another vaccinate which might not be immunized at the time of vaccination. The environmental controls were housed in the same area but kept physically separate from the vaccinates. These animals were bled periodically throughout the observation time and euthanized at day 21. Intestinal scraping impression slides were made and evaluated by direct fluorescent antibody staining. Serological evaluation of the serum samples drawn and evaluation of the intestinal scraping impression slides determined whether environmental exposure to a Canine Corona virus had occurred.

At 21 days after vaccination the vaccinates and controls were anesthetized, bled and challenged intranasally-orally with virulent challenge. The challenge virus was titered to determine the virus input. The vaccinates, controls and challenge sentinel controls were housed in the same building. The vaccinates and controls were monitored daily for temperature elevation, lymphopenia, leukopenia and other symptoms of Corona-induced disease.

A random selection of vaccinates and controls was performed for euthanizing and evaluation of the degree of challenge virus replication in the intestinal tract on days 5, 6 and 7 following challenge. The challenge sentinel controls were euthanized and slides of intestinal tract scrapings examined on days 6 and 7.

All test animals were housed in rooms where the temperature ranged from 50°-70° F. following challenge.

Results

A. Virus Input (See Table 1)

Ten replicate titrations were performed on the virus used to vaccinate the initial set of vaccinates. A geometric mean titer of 2.9 logs of virus was used.

B. Comparison of Antibody Response and Overall Geometric Means

A geometric mean titer of 1:138,491 was obtained by the subcutaneous route of vaccination. The intramuscular route of inoculation elicited a geometric mean serological response of 1:113,761. No significant difference was evident between the routes of administration and the serological response obtained.

C. Vaccine Sentinel Controls (See Tables 7 and 8)

The three dogs used as sentinel controls were shown seronegative at day 0 and at the conclusion of the study. These three dogs were sacrificed and their intestinal tracts examined for infection by the fluorescent antibody staining of intestinal scraping impression slides. The eighteen samples examined for each animal were negative for Canine Corona virus.

It was concluded no "wild type" Canine Corona virus contaminated the facility to invalidate the study.

D. Titration of the Challenge Virus

An isolate of Canine Corona virus was obtained for intranasal oral administration to each vaccinate and challenge control dog. A geometric mean of 5.47 logs per ml was obtained from 7 titrations. Each animal received 2 ml of virus intranasally and 3 ml orally. Therefore, each animal was challenged with 6.2 logs of virus.

E. Observations and Evaluations Following Challenge

1. Temperature Response

One hundred thirty-one observations were made for the subcutaneously and intramuscularly vaccinated groups. No temperature response greater than 103° F. was observed.

Fifty-seven temperature observations were made on the challenge control dogs. A total of 6 observations or 9.5% of the observations were over 103° F. These temperatures were 103.2, 103.2, 103.4, 103.6, 104.0, and 105.0, respectively.

The small degree of temperature response noted in the challenge control dogs was not present in the vaccinates.

2. White Blood Cell (WBC) Response

No significant drop in WBC was observed in either vaccinate or challenge control dogs.

3. Lymphocyte Response

There appeared to be a significant drop in lymphocytes for the challenge control dogs. Seven of ten challenge control dogs or 70% had lymphocyte drops of greater than or equal to 60%. Only three of the vaccinates challenged (13%) had a lymphocyte decrease of over 60% which was 5.2 fold less in the vaccinates; a 2.7 fold less drop in lymphocytes in the vaccinates was observed when considering a lymphocyte drop of 35% or greater and a 2.16 fold less drop in lymphocytes in vaccinates was observed when considering a lymphocyte drop of 25% or greater.

The data indicate that the challenge virus did have an effect on the challenge control dogs and that the vaccination prevented such a severe drop in lymphocytes in the immunized animals.

4. Symptoms of Disease

The symptoms of disease noted in this challenge experiment were not as prevalent as in previous experimentation. However, the challenge control dogs did demonstrate more symptoms than did the vaccinate group. A symptom of disease index was devised by dividing the number of symptoms observed per test group by the total number of observations made. For example, 3 symptoms were observed in the intramuscularly vaccinated dogs. A total of 61 observations were made. Therefore, the symptoms index was 3/61 or 0.049. Table 7 summarizes the symptom index per group.

TABLE 7

| TEST GROUP | OBSERVED SYMPTOMS | NUMBER OF OBSERVATIONS | SYMPTOM INDEX |
|---|---|---|---|
| Combined Vacc. | 7 | 131 | 0.053 |
| Controls | 42 | 57 | 0.737 |

A reduction in the symptom index of 92.8% was obtained when comparing the combined vaccinate group with the challenge control dogs. Although the symptoms of disease were not plentiful in the control animals, the vaccine did significantly prevent as many symptoms in the immunized animals.

Each of the ten challenge control animals demonstrated symptoms so the symptom index does not reflect a severe disease syndrome in just a few control dogs. Seven of the twenty-three vaccinates demonstrated one symptom of disease each.

5. Intestinal Infection—Evaluation by FA Impression Smear Procedure

The evaluation of the degree of infection of the intestinal tract by challenge virus in the control dogs and vaccinates is the most critical parameter for determining the effectiveness of a Canine Corona virus vaccine. Intestines were removed and gently washed in cool tap water. The sections were opened with a scalpel and scrapings were taken. Scrapings were placed directly or exfoliated on glass slides from the intestinal epithelium of the test animals. Sampling occurred at approximately the same location on each animal. The slides were fixed twice in 100% acetone at 25° C. for 30 minutes. Specifically labeled Canine Corona virus conjugate was used to stain each slide for 1 hour at 37° C. The slides were washed in a carbonate buffer wash and observed with a 50 W mercury (HBO) light source. The results are presented in Tables 8-12. Each field was observed and a negative to 4+ fluorescent value was given.

TABLE 8

OBSERVATIONS OF INTESTINAL SCRAPINGS IMPRESSION SLIDES ON CHALLENGE CONTROL DOGS

| Days Post Chal- lenge | No. of Sam- ples | No. of Samples per Degree of FA+ | | | | | % of FA+ | In- fective Index |
|---|---|---|---|---|---|---|---|---|
| | | 4+ | 3+ | 2+ | 1+ | 0 | | |
| 5 | 15 | 2 | 0 | 12 | 0 | 1 | 93.3 | 2.13 |
| 5 | 15 | 0 | 0 | 11 | 1 | 4 | 73.3 | 1.47 |
| 5 | 15 | 2 | 0 | 11 | 0 | 2 | 86.7 | 2.0 |
| 5 | 15 | 0 | 0 | 12 | 0 | 3 | 80.0 | 1.6 |
| 6 | 15 | 5 | 0 | 7 | 0 | 3 | 80.0 | 2.26 |
| 6 | 15 | 4 | 0 | 8 | 0 | 3 | 80.0 | 2.13 |
| 6 | 15 | 8 | 0 | 3 | 0 | 4 | 73.3 | 2.53 |
| 7 | 15 | 10 | 0 | 0 | 0 | 5 | 66.7 | 2.67 |
| 7 | 15 | 10 | 0 | 2 | 0 | 4 | 80.0 | 2.93 |
| 7 | 15 | 14 | 0 | 0 | 0 | 1 | 93.3 | 3.73 |
| Total | | 64 | 0 | 66 | 1 | 30 | 889.9 | 23.45 |
| Avg. | | 6.4 | | 6.6 | | 3.0 | 88.99 | 2.345 |

TABLE 9

Observation of Intestinal Scraping Impression Slides On Dogs Euthanized 5 Days After Challenge

| Vaccin- ate or Control | Route of Vaccina- tion | No. of Samples | No. of Samples per Degree of FA+ | | | | | % of FA+ | Infective Index |
|---|---|---|---|---|---|---|---|---|---|
| | | | 4+ | 3+ | 2+ | 1+ | 0 | | |
| V | SC | 15 | 0 | 0 | 0 | 2 | 13 | 13 | 0.13 |
| V | SC | 15 | 0 | 0 | 0 | 3 | 12 | 20 | 0.20 |
| V | SC | 15 | 0 | 0 | 0 | 0 | 15 | 0 | 0 |
| V | SC | 15 | 0 | 0 | 0 | 1 | 14 | 6 | 0.06 |
| V | IM | 15 | 0 | 0 | 0 | 2 | 13 | 13 | 0.13 |
| V | IM | 15 | 0 | 0 | 0 | 2 | 13 | 13 | 0.13 |
| V | IM | 15 | 0 | 0 | 0 | 0 | 15 | 0 | 0 |
| C | — | 15 | 2 | 0 | 12 | 0 | 1 | 93.3 | 2.13 |
| C | — | 15 | 0 | 0 | 11 | 0 | 4 | 73.3 | 1.47 |
| C | — | 15 | 2 | 0 | 11 | 0 | 2 | 86.7 | 2.00 |
| C | — | 15 | 0 | 0 | 12 | 0 | 3 | 80 | 1.6 |

TABLE 10

Observation of Intestinal Scraping Impression Slides On Dogs Euthanized 6 Days After Challenge

| Vaccin- ate or Control | Route of Vaccina- tion | No. of Samples | No. of Samples per Degree of FA+ | | | | | % of FA+ | Infective Index |
|---|---|---|---|---|---|---|---|---|---|
| | | | 4+ | 3+ | 2+ | 1+ | 0 | | |
| V | SC | 15 | 0 | 0 | 0 | 1 | 14 | 6.7 | .067 |
| V | SC | 15 | 0 | 0 | 0 | 0 | 15 | 0 | 0 |
| V | SC | 15 | 0 | 0 | 0 | 5 | 10 | 33.3 | 0.33 |
| V | SC | 15 | 0 | 0 | 0 | 4 | 11 | 26.7 | 0.267 |
| V | IM | 15 | 0 | 0 | 0 | 0 | 15 | 0 | 0 |
| V | IM | 15 | 0 | 0 | 0 | 0 | 15 | 0 | 0 |
| V | IM | 15 | 0 | 0 | 0 | 0 | 15 | 0 | 0 |
| V | IM | 15 | 0 | 0 | 0 | 0 | 15 | 0 | 0 |
| C | — | 15 | 5 | 0 | 7 | 0 | 3 | 80.0 | 2.27 |
| C | — | 15 | 4 | 0 | 8 | 0 | 3 | 80.0 | 2.13 |
| C | — | 15 | 8 | 0 | 3 | 0 | 4 | 73.3 | 2.53 |
| Sentinel Control | — | 15 | 0 | 0 | 0 | 0 | 15 | 0 | 0 |

TABLE 11

Observation of Intestinal Scraping Impression Slides On Dogs Euthanized 7 Days After Challenge

| Vaccin- ate or Control | Route of Vaccina- tion | No. of Samples | No. of Samples per Degree of FA+ | | | | | % of FA+ | Infective Index |
|---|---|---|---|---|---|---|---|---|---|
| | | | 4+ | 3+ | 2+ | 1+ | 0 | | |
| V | SC | 15 | 0 | 0 | 0 | 1 | 14 | 6.67 | .067 |
| V | IM | 15 | 0 | 0 | 0 | 8 | 7 | 53.3 | .533 |
| V | IM | 15 | 0 | 0 | 0 | 2 | 13 | 13.3 | .133 |

TABLE 11-continued

Observation of Intestinal Scraping Impression Slides
On Dogs Euthanized 7 Days After Challenge

| Vaccinate or Control | Route of Vaccination | No. of Samples | No. of Samples per Degree of FA+ | | | | | % of FA+ | Infective Index |
|---|---|---|---|---|---|---|---|---|---|
| | | | 4+ | 3+ | 2+ | 1+ | 0 | | |
| V | IM | 15 | 0 | 0 | 0 | 3 | 12 | 20.0 | .2 |
| V | IM | 15 | 0 | 0 | 0 | 0 | 15 | 0 | 0 |
| V | IM | 15 | 0 | 0 | 0 | 0 | 15 | 0 | 0 |
| V | IM | 15 | 0 | 0 | 0 | 0 | 2 | 13 | .133 |
| C | — | 15 | 10 | 0 | 0 | 0 | 5 | 66.7 | 2.67 |
| C | — | 15 | 10 | 0 | 0 | 2 | 3 | 80 | 2.93 |
| C | — | 15 | 14 | 0 | 0 | 0 | 1 | 93.3 | 3.73 |
| Sentinel Control | — | 15 | 0 | 0 | 0 | 0 | 15 | 0 | 0 |

TABLE 12

Infective Index Comparison Indicating Reduction in Intestinal Infection

| Test Group | Infective Index per Day of Euthanizing | | |
|---|---|---|---|
| | 5 | 6 | 7 |
| SC Vaccinates | 0.0975 | 0.132 | 0.067 |
| IM Vaccinates | 0.13 | 0 | 0.217 |
| Combined Groups | 0.108 | 0.066 | 0.187 |
| Challenge Controls | 1.8 | 2.31 | 3.11 |
| Percent Reduction Combined Group vs Controls | 94% | 97% | 94% |

The challenge control infective index ranged from 1.47 to 3.73 with an average of 2.345, whereas the combined vaccinate group of 22 dogs had an infective index of 0.103. These data indicate that a reduction of intestinal infection of 95.6% was achieved in the vaccinates.

EXAMPLE 6

CANINE CORONA VIRUS AS A COMBINATION PRODUCT

A pilot serial of vaccine was batched with Canine Corona virus and Canine Parvo virus as components as follows:

| CCV fluids | 4.5 liters |
|---|---|
| CPV fluids | 2.0 liters |
| Stabilizer | 2.2 liters |
| Fetal Calf Serum | 0.1 liters |
| 1 N NaOH | 0.08 liters |

The materials were blended under refrigeration and bottled aseptically in a 1 ml dose. The bottles of vaccine were then subjected to desiccation. The virus yields were as follows:

| CCV | $10^{5.4}$ FAID$_{50}$/dose |
|---|---|
| CPV | $10^{6.5}$ FAID$_{50}$/dose |

It is quite feasible to routinely produce and batch CCV as a combination product.

This portion of the study was designed to determine if antigen interference would occur when Canine Corona virus and Canine Parvo virus were combined for administration as a combination vaccine.

The experimental design can be found in Table 13. Three groups of dogs were used. Group I was vaccinated with a full field dose of Canine Corona virus vaccine (1 ml). Group II was vaccinated with a full field dose of Canine Corona-Parvo virus Vaccine (1 ml). The third group was vaccinated with a full field dose of Canine Parvo virus (1 ml). Portions of each group were vaccinated intramuscularly (IM) while the remaining dogs were vaccinated subcutaneously (SC). The dogs were bled on day 0 and also 21 days after vaccination. Sentinel controls were also bled on day 0 and day 21.

TABLE 13

Antigen Blockage Study Experimental Design

| Treatment | Group I | Group II | Group III |
|---|---|---|---|
| Prevaccination Bleeding and Vaccination (day 0) | 4 vaccinated SC<br>4 vaccinated IM | 3 vaccinated SQ<br>5 vaccinated IM | 3 vaccinated SQ<br>4 vaccinated IM |
| Post vaccination bleeding (day 21) | bled | bled | bled |

Five replicate titrations were performed on each virus fraction. The data indicate a virus input of 4.5 logs of Corona virus for group I, 5.5 logs of Canine Parvo virus for group III, and 4.4 logs of Canine Corona virus with 5.5 logs of Canine Parvo virus for group II.

1. Test Group I—Canine Corona virus Vaccinate

The data indicated that a geometric mean titer of 1:6498 is obtained against Canine Corona virus.

2. Test Group II—Canine Corona-Parvo virus Vaccinate

The dogs in test Group II responded to a geometric mean titer of 1:87,222 against Canine Corona virus and a geometric mean titer of 1:58,579 against Canine Parvo virus 21 days after receiving 1 field dose of vaccine.

3. Test Group III—Canine Parvo virus Vaccinate

A geometric mean titer of 1:65,893 was obtained in this test group against Canine Parvo virus.

The results are summarized in Table 14.

TABLE 14

Post Serological Canine Corona and Parvo Response Arithmetic and Geometric Means Summary

| Group | Vaccine | Post Vaccination Antibody Titer | | | |
|---|---|---|---|---|---|
| | | AM* | | GM** | |
| | | CCV | CPV | CCV | CPV |
| I | CCV | 64,111 | — | 6,498 | — |
| II | CCV-CPV | 163,436 | 128,172 | 87,222 | 58,579 |
| III | CPV | — | 391,982 | — | 65,893 |

*Arithmetic Mean
**Geometric Mean

Analysis for Antigen Blockage (a) Canine Corona virus (See Table 14)

No antigen blockage was noted for the Canine Corona virus. A geometric mean antibody titer of 1:87,222 was achieved with the combination product as compared to a geometric mean antibody level of 1:6498 with the monovalent product against Canine Corona virus. A potentiation effect is achieved with the Canine Corona virus in combination. A 13.4 fold increase in Canine Corona virus antibody titer is realized when comparing the combination product to the monovalent product.

(b) Canine Parvo virus

There was no significant difference in antibody titers against Canine Parvo virus when comparing the combination product with the monovalent product. A geometric mean titer of 1:58,579 with the combination product compares well with a geometric mean titer of 1:65,893 with the monovalent product. No antigen blockage was observed.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A vaccine composition comprising: a member selected from the class consisting of inactivated canine coronavirus and modified live canine coronavirus in an amount of at least 1000 virus particles per dose as measured by the $FAID_{50}$ method; and a non-toxic pharmaceutically acceptable carrier.

2. The composition of claim 1 wherein said carrier in an aqueous solution suitable for parenteral injection.

3. The composition of claim 2 wherein said canine coronavirus is modified live canine coronavirus.

4. The composition of claim 2 wherein said canine coronavirus is inactivated canine coronavirus.

5. The composition of claim 2 which further includes at least one canine virus vaccine selected from the group consisting of canine parvovirus vaccine, canine distemper virus vaccine, canine parainfluenza virus vaccine, canine adenovirus I vaccine and canine adenovirus II vaccine.

6. A method for protecting dogs from infection caused by canine coronavirus comprising: administering to a dog a vaccine composition containing a member selected from the class consisting of inactivated canine coronavirus and modified live canine coronavirus in an amount sufficient to protect said dog from infection by virulent canine coronavirus of at least 2.5 logs of virus particles per dose as measured by the $FAID_{50}$ method.

7. The method of claim 6 wherein said vaccine composition is parenterally administered in an amount of at least 1000 virus particles per dose as measured by the $FAID_{50}$ method and wherein the protection afforded is a reduction of at least eighty percent in intestinal infection.

8. The method of claim 7 wherein said vaccine composition contains modified live canine coronavirus.

9. The method of claim 8 wherein said vaccine composition further includes at least one canine virus vaccine selected from the group consisting of canine parvovirus vaccine, canine distemper virus vaccine, canine parainfluenza virus vaccine, canine adenovirus I vaccine and canine adenovirus II vaccine.

10. The method of claim 7 wherein said vaccine composition contains inactivated canine coronavirus.

11. The method of claim 10 wherein said vaccine composition further includes at least one canine virus vaccine selected from the group consisting of canine parvovirus vaccine, canine distemper virus vaccine, canine parainfluenza virus vaccine, canine adenovirus I vaccine and canine adenovirus II vaccine.

12. A vaccine composition comprising a member selected from the class consisting of inactivated canine coronavirus ATCC No. VR 2068 and modified live canine coronavirus ATCC No. VR 2068 present in an amount of at least 2.5 logs of virus particles per dose as measured by the $FAID_{50}$ method; and a non-toxic pharmaceutically acceptable carrier.

13. The vaccine composition of claim 12 comprising: canine coronavirus present in an amount of at least 1000 virus particles per dose as measured by the $FAID_{50}$ method; and a non-toxic pharmaceutically acceptable carrier.

14. The composition of claim 12 wherein said canine coronavirus ATCC No. VR 2068 is inactivated.

15. The vaccine composition of claim 12 which further includes a canine parvovirus vaccine.

16. The vaccine composition of claim 12 which further includes at least one canine virus vaccine selected from the group consisting of Canine Distemper virus vaccine, Canine Parainfluenza virus vaccine, Canine Adenovirus I vaccine, and Canine Adenovirus II vaccine.

17. The composition of claim 12 wherein said carrier is an aqueous solution suitable for parenteral injection.

18. The composition of claim 12 wherein said canine coronavirus is modified live canine coronavirus ATCC No. VR 2068.

19. The composition of claim 18 wherein said canine coronavirus is present in amount of at least 3.3 logs of virus particles per dose as measured by the $FAID_{50}$ method.

20. The method for protecting dogs from infection caused by canine coronavirus comprising: administering to a dog a vaccine composition containing a member selected from the class consisting of inactivated canine coronavirus ATCC No. VR 2068 and modified live canine coronavirus ATCC No. VR 2068, in an amount of at least 1,000 virus particles per dose as measured by the $FAID_{50}$ method.

21. The method of claim 20 wherein said vaccine composition is administered intramuscularly.

22. The method of claim 20 wherein said vaccine composition is administered subcutaneously.

23. The method of claim 20 wherein said vaccine composition is parenterally administered whereby both humoral systemic immunity and local immunity in the intestinal tract are induced.

* * * * *